July 2, 1957 M. L. WHISLER Plant Pat. 1,615
ROSE PLANT
Filed Oct. 29, 1956
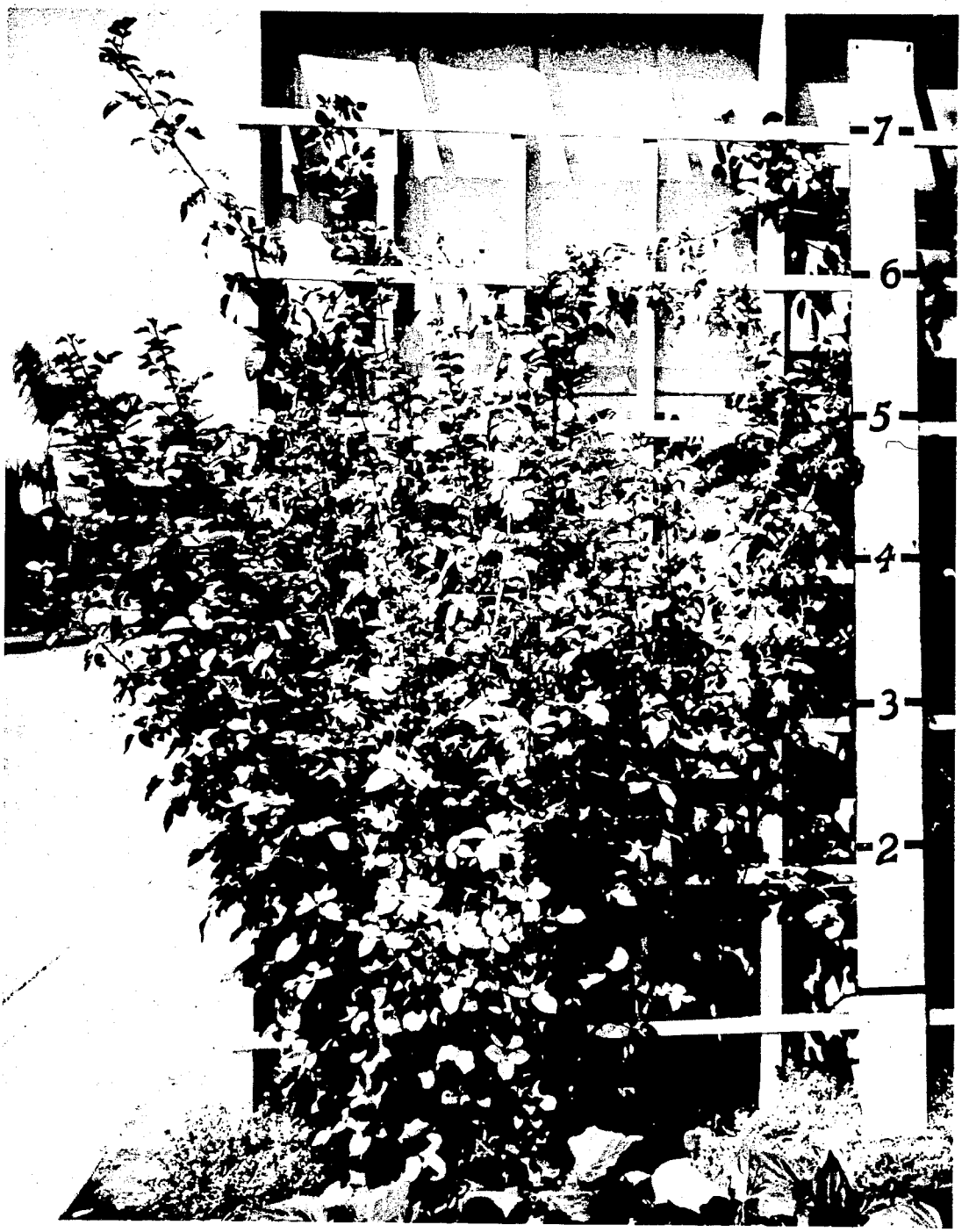
Inventor.
M. L. Whisler
By: Robb & Robb
Attorneys.

United States Patent Office

Plant Pat. 1,615
Patented July 2, 1957

1,615

ROSE PLANT

Milton L. Whisler, Granada Hills, Calif., assignor to Germain's, Inc., Van Nuys, Calif., a corporation of California Application October 29, 1956, Serial No. 619,095

1 Claim. (Cl. 47—61)

The present invention relates to a new and distinct variety of rose plant of the climber class, which was discovered by me as a bud sport of the variety "Queen Elizabeth" (Plant Patent No. 1,259), but which is distinguished from the latter parent variety by its climbing habit of growth. The new variety was discovered by me amongst a cultivated block of "Queen Elizabeth" plants which were being grown under my direction and supervision at Saugus, California, on property controlled by my assignee.

At the time of my discovery, my attention was attracted to the new variety by the unusually vigorous and climbing habit of a particular plant of the "Queen Elizabeth" variety in the block of plants mentioned above. Upon closer examination thereof, I found that the parent plant had sported, and I thereupon promptly took steps to preserve, asexually reproduce and observe this sport for the purpose of determining whether or not its climbing habit was fixed and transmissible by asexual reproduction. The climbing habit was fully confirmed by such observations and by asexual reproduction by budding, as performed by me at Saugus, California, and I have therefore established that the climbing habit of growth of the new variety comes true to form and is transmissible through succeeding propagations.

The parent variety ("Queen Elizabeth") is a bush rose of the hybrid tea class, and is primarily notable for its unusual vigor and upright habit of growth, its large, leathery, glossy, dark green leaves and the abundance thereof, its abundant production of flowers which are borne on relatively long cutting stems, and by the unusually clear Carmine Rose to Dark Pink general color tonality of its flowers which shade to lighter shades of Carmine Rose to Dark Pink, with the outer portions of the petals becoming heavily peppered with Carmine where the sunlight strikes strongest. This bush variety, so far as I am aware, has never exhibited a climbing habit, and its growth has usually been of the average strong bush rose. The new variety herein is substantially identical to its parent in all respects, except that it is definitely a climber, and like its parent, the plant is heavily clothed with large, leathery, dark green foliage, and is very floriferous.

In view of the general similarities between my new variety and its parent, except as noted above, it is unecessary to describe or illustrate the new variety in detail, since it otherwise substantially conforms to the detailed description and illustration embodied in Plant Patent No. 1,259, dated February 23, 1954, to which reference may readily be had, but for convenience, the accompanying drawing illustrates in black-and-white a typical specimen plant of my new variety in association with a marked scale graduated in feet to denote the relative height of the plant, and in the following portion of this application, there is given a brief description of the new variety, with color terminology in accordance with the Horticultural Color Chart of the British Color Council, except where general color terms of ordinary dictionary significance are obvious:

Type: Hardy; climber; for cut flowers and for garden decoration.

Class: Hybrid tea.

Parentage: Sport of "Queen Elizabeth."

Propagation: Holds its distinguishing characteristics through succeeding propagations by budding.

*Flower*

Locality where grown and observed: Saugus, California.

Flowers borne: Usually singly, but occasionally two or three to stem; on strong, long stems.

Quantity of bloom: Abundant, outdoors.

Continuity: Continuous.

Fragrance: Moderate. Nature—centifolia.

Bud:

*Peduncle.*—Medium length; heavy; erect; stiff; entirely smooth; few gland-tipped hairs, but no prickles or thorns. Color—greenish-bronze.

*Before calyx breaks.*—Size—medium. Form—medium length; pointed; with foliaceous appendages on the edges of alternate sepals varying from ⅛ inch to ⅜ inch long and from 1/16 inch to ⅛ inch wide, said appendages being lance-shaped. Color—from Carmine, Plate 21, to Carmine, Plate 21/1.

*As calyx breaks.*—Color—Carmine, Plate 21/2, with streak of China Rose, Plate 024, near mid-rib.

*As first petal opens.*—Size—medium. Form—pointed. Color: outside—from Crimson, Plate 22/2, to Neyron Rose, Plate 623/1; inside—Carmine Rose, Plate 621/2.

*Opening.*—Opens up well.

Bloom:

*Size (when fully open).*—From 3½ inches to 4 inches.

*Petalage.*—From 37 to 40 petals; arranged regularly.

*Form.*—Very high-centered at first, but becoming cupped; petals being at first rolled inward, but becoming loosely rolled outward later at maturity; very regularly imbricate petal arrangement, with inner petals and petaloids rolled inward and covering stamens.

*Petals.*—Texture—medium thin; with both inside and outside satiny. Shape: outside—obovate, with apex 1/16 inch long; no notches; intermediate—obovate; usually with one notch, but occasionally some with short apex.

This description of a newly opened flower was made from a rose grown outdoors in the month of September at Saugus, California:

*Color.*—Outer petal: outside surface—Neyron Rose, Plate 623/1; inside surface—Carmine Rose, Plate 621/2. Intermediate petal: outside surface—Neyron Rose, Plate 623/2; inside surface—Dawn Pink, Plate 523/1. Inner petal: outside surface—Neyron Rose, Plate 623/2; inside surface—Dawn Pink, Plate 523/2.

This description was made from a rose that was open for 3 days outdoors in the month of October, at Saugus, California:

*Color.*—Outer petal: outside surface—Neyron Rose, Plate 623/2; inside surface—Carmine Rose, Plate 621/3. Inner petal: outside surface—Neyron Rose, Plate 623/3; inside surface—Dawn Pink, Plate 523/3 at base, but peppered with Carmine, Plate 21/2 on outer margin where sun strikes strongest.

*General color effect.*—Newly opened flower—from Carmine Rose to Dawn Pink. 3-days open—lighter shades of from Carmine Rose to Dawn Pink and strongly influenced by peppered effect of Carmine on outer part of petals.

*Behavior.*—Drop off cleanly; affected very little by heat or cold.

*Flower longevity.*—On bush in garden—5 days in October. Cut flowers grown outdoors and kept at livingroom temperatures—6 days in October.

*Reproductive organs*

Stamens: Medium number; arranged irregularly about pistils.

Filaments: Some short, but mostly medium length; most with anthers. Color—French Rose, Plate 520.

Anthers: Medium size; open at various times. Color—Majolica Yellow, Plate 09.

Pollen: Moderate. Color—gold.

Pistils: Medium number.

Styles: Uneven; medium length; medium caliper; bunched. Color (upper part)—Claret Rose, Plate 021.

Stigma: Color—yellow.

Ovaries: All enclosed in calyx.

Hips: Globular; with inconspicuous neck; smooth; thin walls. Color—yellow.

Sepals: Falling soon; recurved. Color—Willow Green, Plate 000862/2.

*Plant*

Foliage:

*Leaves.*—Compound of 5 to 7 leaflets; abundant; moderately large; heavy; leathery; glossy.

*Leaflets.*—Shape—elliptical, with round base. Margin—simply serrate.

*Color.*—Mature: upper surface—near Parsley

Green, Plate 00962; under surface—near Spinach Green, Plate 0960/3. Young: upper surface—Parsley Green, Plate 00962/1 at base, tinged with Pansy Purple, Plate 928; under surface—Spinach Green, Plate 0960/2, strongly tinged with Pansy Purple, Plate 928.

*Rachis (the supporting stem of the compound leaf).*—Heavy. Upper side—smooth; grooved. Under side—smooth, but occasionally with one small thorn at each leaf junction and occasionally between leaf junctions.

*Stipules.*—Short; narrow; with short points turning out at an angle of 45°.

*Disease resistance.*—Resistant to mildew, as determined by comparison with susceptible varieties grown nearby under comparable cultural conditions and which were heavily infested with mildew, at Saugus, California.

Growth:

*Habit.*—Climber.

*Growth.*—Very vigorous.

*Canes.*—Heavy.

*Main stems.*—Color—Parsley Green, Plate 00962/2. Thorns—several; medium length; with long, narrow base. Prickles—none. Hairs—none.

*Branches.*—Color—Parsley Green, Plate 00962/2. Thorns—several; medium length; straight; with long, narrow, ovate base. Prickles—none. Hairs—none.

*New shoots.*—Color—Spinach Green, Plate 0960/2, overlaid Garnet Brown, Plate 00918. Thorns—several; medium length; straight; with long, narrow base. Prickles—none. Hairs—none.

I claim:

A new and distinct variety of rose plant of the climbing hybrid tea class, substantially as herein shown and described, characterized particularly as to novelty by being substantially identical with its parent variety "Queen Elizabeth" (Plant Patent No. 1,259), including the latter's foliaceous habit and abundant, large, leathery, dark-green foliage which heavily clothes the plant, but being essentially distinguished therefrom by its vigorous and climbing habit of growth.

No references cited.